United States Patent
Gregory, Jr.

(10) Patent No.: US 6,187,017 B1
(45) Date of Patent: Feb. 13, 2001

(54) RETRIEVAL BASKET FOR A SURGICAL DEVICE

(75) Inventor: Franklin P. Gregory, Jr., Racine, WI (US)

(73) Assignee: Circon Corporation, Santa Barbara, CA (US)

( * ) Notice: Under 35 U.S.C. 154(b), the term of this patent shall be extended for 0 days.

(21) Appl. No.: 09/025,099

(22) Filed: Feb. 17, 1998

(51) Int. Cl.$^7$ ........................................... A61B 17/22
(52) U.S. Cl. ......................................................... 606/127
(58) Field of Search ........................ 606/127, 114

(56) References Cited

U.S. PATENT DOCUMENTS

| | | |
|---|---|---|
| 4,425,908 | 1/1984 | Simon . |
| 5,057,114 | 10/1991 | Wittich et al. . |
| 5,133,733 | 7/1992 | Rasmussen et al. . |
| 5,330,482 | 7/1994 | Gibbs et al. . |
| 5,484,384 | 1/1996 | Fearnot . |
| 5,792,145 * | 8/1998 | Bates et al. ........................ 606/127 |

FOREIGN PATENT DOCUMENTS

| | | |
|---|---|---|
| 0 123 175 | 9/1986 | (EP) . |
| 391384 * | 10/1990 | (EP) ..................................... 606/127 |
| 0 160 870 | 7/1991 | (EP) . |
| 240173 * | 3/1969 | (SU) ..................................... 606/127 |
| WO 92/16153 | 10/1992 | (WO) . |
| WO 96/15728 | 5/1996 | (WO) . |

OTHER PUBLICATIONS

English translation of Russian Patent No. 240173 of V.P. Pashkovskiy for Gallstone Extractor.

* cited by examiner

Primary Examiner—Jeffrey A. Smith
(74) Attorney, Agent, or Firm—Bradley M. Ganz, Esq

(57) ABSTRACT

A retrieval basket is provided for use with a surgical device adapted to capture calculi. The retrieval basket includes wires extending from a proximal end to a distal end of the basket wherein the wires converge at the proximal and distal ends. The wires in a proximal portion of the retrieval basket incline radially at an angle away from the basket's axis along relatively straight paths. The wires in a distal portion of the retrieval basket converge radially toward the axis along relatively curvilinear paths.

56 Claims, 5 Drawing Sheets

RETRIEVAL BASKET FOR A SURGICAL DEVICE

BACKGROUND OF THE INVENTION

This invention provides a retrieval basket for use with a surgical device. In particular, it provides a basket adapted to capture calculi for removal from a surgical patient.

FIELD OF THE INVENTION

There is an ongoing demand for improved surgical devices that are capable of removing objects from a surgical patient's body. In the fields of urology and gastroenterology, for example, there is a demand for improved devices that are capable of capturing and retrieving calculi. Calculi in the urinary tract, commonly composed of calcium oxalate for example, cause pain whether they are positioned in the kidney or bladder or elsewhere and can be especially painful as they pass through a duct such as the ureter. Such calculi (or "stones") often need to be removed surgically to avoid or to cure a urinary obstruction and possible infection.

Various retrieval baskets have been proposed over the years for calculi removal. They generally include wires formed to define a "cage" in an expanded position into which calculi can be maneuvered. A sheath is often provided to maintain the wires in a collapsed position for insertion. A handle is often provided for manipulation of the sheath and basket with respect to one another in order to move the basket or cage between the collapsed and expanded positions. In use, the basket is advanced distally to a position within the patient's duct that is beyond a calculus to be grasped while the basket is in the collapsed position within the sheath. It is subsequently expanded upon release from the sheath and drawn back proximally to capture the calculus.

So-called "flat-wire baskets," such as the SURLOK Flat-Wire Stone Baskets offered by CIRCON SURGITEK (Part Nos. 57100XX), have been introduced to engage stones. They are formed from wires that are substantially straight and parallel to one another throughout the basket's length. Flat-wire baskets have been found to be advantageous in that a calculus captured within the basket can be deployed or released in some cases from the basket by the surgeon, if desired. Such release may be advantageous if the calculus cannot be extracted from the patient, i.e., if the calculus is too large or oversized in some dimension for easy extraction from a patient.

Despite the advantages of flat-wire baskets, it has been discovered in some instances that certain calculus shapes might not be easily grasped. Specifically, it has been discovered that the parallel wires of the basket define gaps that extend along the basket's length and that calculi can escape capture in some instances if they are aligned with one of these gaps as the basket is drawn back to grasp the calculi.

So-called "helical baskets", such as the SURLOK Helical Stone Baskets provided by CIRCON SURGITEK (Part Nos. 57000XX), have also been introduced for calculi retrieval. Such helical retrieval baskets generally include wires that are formed into a helical configuration. They have been discovered to be advantageous in that they are extremely effective for capturing calculi for extraction and for securely retaining the captured calculi within the basket. Despite this significant advantage of conventional helical baskets, it has been discovered in some instances that they grasp calculi so well that it may become difficult to deploy or release a captured calculus from the basket if it is discovered to be too large for easy extraction from the patient.

U.S. Pat. No. 4,347,846 issued to Enrico Dormia describes a surgical extractor having a basket formed by wires arranged in pairs and disposed in helical paths wherein one wire of each pair is spiralled in a clockwise direction and the other in a counter-clockwise direction so that the wires of each pair intersect at a single point. The points of intersection are intended to constitute zones where the calculus body will be definitely imprisoned, being held firmly, without risk of escape.

Another example of a basket is described by James Bates et al. in U.S. Pat. No. 5,496,330. It includes pairs of wires that are expanded such that each pair of wires closely assumes a path along a helical turn with individual wires remaining closely adjacent throughout the length of the basket. The object was to provide a surgical extractor that increases the number of contact points with calculi in a retrieval basket to increase the reliability with which the retrieval basket entraps calculi.

OBJECT OF THE INVENTION

It is an object of this invention to provide an improved retrieval basket for a surgical device that overcomes the drawbacks of conventional baskets.

It is another object of this invention to provide a retrieval basket that is adapted to capture calculi securely yet may also be capable of releasing captured calculi, if desired.

Other objects and advantages of the invention will become clear in view of the following description.

SUMMARY OF THE INVENTION

This invention provides a retrieval basket adapted to capture calculi securely yet can also be adapted to release captured calculi, if desired. It includes a plurality of wires extending between the proximal and distal ends of the basket. The wires diverge radially away from the basket's axis along relatively straight or relatively parallel paths in a proximal portion of the retrieval basket. The wires also converge radially toward the basket's axis along substantially curvilinear paths, preferably helical, in the distal portion of the retrieval basket.

Each wire extends from the basket's proximal end and in a proximal portion of the basket closely adjacent to another wire and then diverges from the other wire at a location spaced from the basket's proximal end. Adjacent wires can either cross one another near the proximal end of the basket before diverging from one another or they can extend substantially parallel to one another near the proximal end without crossing.

The wires can also be formed so that they extend along a so-called "dual helical path" between the expanded basket's proximal and distal ends, wherein the wires extend along a proximal helical path and then extend along a distal helical path that has a smaller radius of curvature as compared to the proximal helical path.

DETAILED DESCRIPTION OF THE INVENTION

Figure 1:
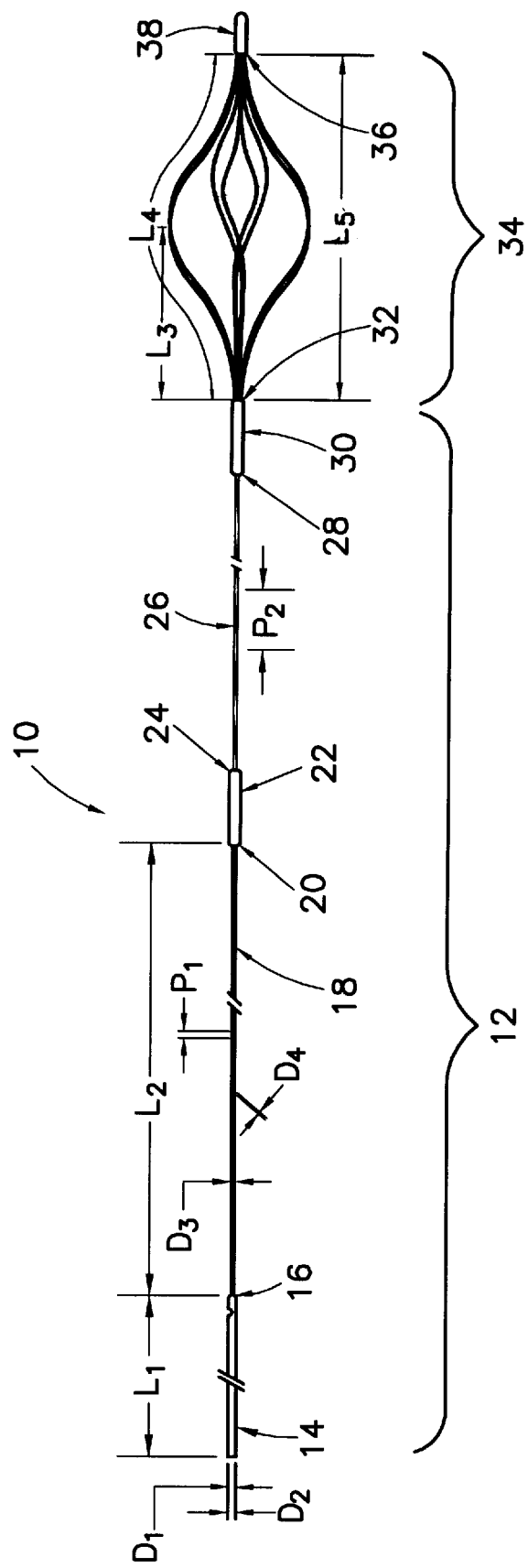
FIG. 1 shows a side view of a surgical device utilizing an embodiment of a retrieval basket according to this invention.

This invention will now be described with reference to several embodiments selected for illustration in the drawings. It will be appreciated that the invention is not limited to the embodiments selected for illustration and that the drawings are not intended to conform to any particular scale. The following description is not intended to limit the scope of the invention, which is defined separately in the appended claims.

This invention is described with reference to surgical devices that are adapted for extraction of calculi from a surgical patient's duct although it is contemplated that other surgical instruments and other applications would benefit from the invention. The handle and shaft components of such a surgical device are not critical to this invention and the handle and shaft components described herein can be interchanged with equivalent or conventional components.

Various handle and shaft arrangements are found in the SURLOK™ Flat-Wire Stone Basket and SURLOK™ Helical Stone Baskets provided by CIRCON SURGITEK. Additional assemblies are described in Dormia U.S. Pat. No. 4,347,846, Bates et al. U.S. Pat. No. 5,496,330, and Fleury et al. U.S. Pat. No. 5,573,530, each of which are incorporated herein by reference. For example, the handle can include a moveable thumb slide basket positioner that is connected to a cable that extends to the basket. The thumb slide permits the advancement and retraction of the basket with respect to the handle. A sheath is fixedly attached to the handle and remains stationary with respect to the handle. Advancement of the basket by means of the thumb slide in the distal direction causes the basket to extend from the end of the sheath so that it expands. Retraction of the thumb slide in the proximal direction retracts the basket into the end of the sheath. Alternatively, the handle can include a mechanism for positioning a moveable sheath and the basket can be fixed with respect to the handle. In such a configuration, advancement of the moveable sheath collapses the basket and retraction of the sheath allows the basket to expand.

Referring now to the retainer basket embodiments selected for illustration in the drawings, FIG. 1 illustrates a portion of a surgical device generally designated by the numeral "10" that incorporates aspects of this invention. It includes an elongated shaft 12 that is preferably flexible but can also be rigid. At a proximal end of shaft 12 (toward the left in FIG. 1) is provided a connector tube 14 formed from stainless steel or another suitable material. Connector tube 14 is provided with a length $L_1$ as well as inner diameter $D_1$ and outer diameter $D_2$ that are adapted for connection within a handle (not shown) as described earlier. Connector tube 14 is connected by means of a solder joint 16 to a twisted wire portion 18. In this embodiment, twisted wire portion 18 includes six strands of wire wrapped around one to provide an overall outer diameter $D_3$, although other wire configurations are contemplated such as braided wires, a solid monofilament, etc. Each wire has a diameter $D_4$ and is twisted with a relatively tight pitch $P_1$ with a large number of turns per unit length extending along a length $L_2$ of portion 18. A solder joint 20 connects twisted wire portion 18 to a connector tube 22 which, in turn, is connected by another solder joint 24 to a relaxed pitched portion 26. Relaxed pitch portion 26 is formed from eight wires in this embodiment twisted in a relatively relaxed pitch $P_2$ with a smaller number of turns per unit length. Relaxed pitch portion 26 is connected by means of another solder joint 28 to a connector tube 30, which is positioned at the proximal end portion of elongated shaft 12 (toward the right side in FIG. 1).

Additional shaft assembly embodiments include the use of flexible tubular or solid non-braided members or plastic-encased metal. Other materials such as nickel-titanium alloy or rigid thermoplastic materials may also be used. Also, joining means other than solder can be used to connect various components of surgical device 10 together, including threaded connections, crimped connections, interference fits and other known joining means.

Connected to shaft 12 by means of a solder joint 32 is a retrieval basket 34 comprised of eight wires, details of which will be provided later. The number of wires used to form the basket may or may not correspond to the number of wires used to form relaxed pitch portion 26, depending on design and manufacturing considerations. Relaxed pitch portion 26 and other portions of shaft 12 can alternatively be formed from a monofilament or hollow or solid rod. As will be described, different quantities of wires can be used to form the basket depending on the intended usage of the basket, the diameters of the wires selected for use in the device and manufacturing and cost considerations. This can be an odd number of wires although an even number is preferred. Also, each "wire" is preferably a slender rod but can also take the form of a grouping of substantially parallel, braided, or twisted strands that share a substantially common path along the length of the basket as opposed to a solid wire.

A solder joint 36 connects a basket tip 38 that defines the distal end of retrieval basket 34 and the distal end of the surgical device 10. The extreme tip of basket tip 38 is preferably rounded or radiused or otherwise shaped to provide for atraumatic contact with the patient. Tip 38 is optionally a short collar. Alternatively, tip 38 is a straight or curved filiform tip that extends distally from the end of basket 34. Such a filiform tip is preferably flexible so that it can be used for guidance of the basket through a patient's body passage and for negotiating and maneuvering the basket past a calculus to be grasped. Various structures and configurations for such filiform tips are known in the art and the exact configuration of such a tip is not critical to this invention.

Retrieval basket 34 has a length $L_3$ between its proximal end at solder joint 32 and a wire pair diverging point which will be described later in more detail. The wires forming the retrieval basket have an overall wire length $L_4$ in the basket and they are configured with a curvature that provides an overall basket length $L_5$ when the basket is in its expanded condition as shown in FIG. 1.

Although not shown, a sheath can be moveably positioned over at least portions of shaft 12 and basket 34 to provide means for alternating or reciprocating basket 34 between an expanded position as shown in FIG. 1, a collapsed position within the sheath wherein the basket's wires are oriented adjacent to the basket's axis, and various positions between the expanded and collapsed positions for capturing a calculus. Alternatively, the sheath can be eliminated.

Figure 2:
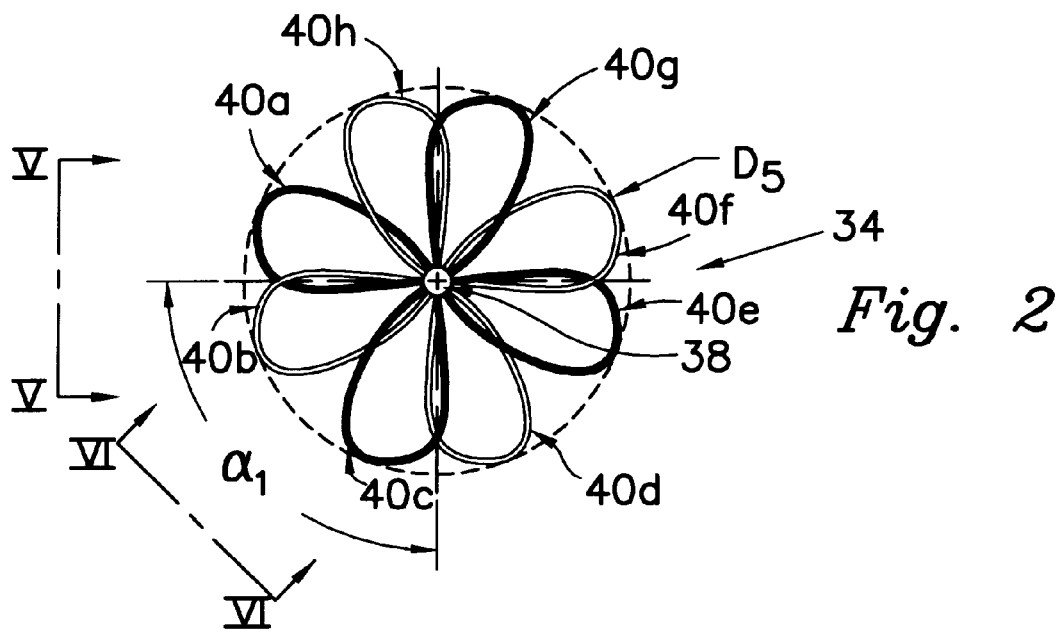
FIG. 2 shows a distal end view of the retrieval basket shown in FIG. 1.

Details of retrieval basket 34 are shown in FIG. 2 in a distal end view. It includes eight wires 40a–40h, which are alternately shown in solid and outline for clarity. As will be described more clearly with reference to FIGS. 4 and 6, the wires of this embodiment are preferably assembled so that they can be considered to be grouped in four pairs at the proximal end having two wires in each proximal pairing, i.e., wires 40a and 40b, wires 40c and 40d, wires 40e and 40f, and wires 40g and 40h. As indicated in phantom, the wires 40a–40h are formed so that they extend outwardly to a maximum achieved diameter $D_5$, which is selected based on the intended use of the basket and the body passages through which it is intended to be inserted. The wires in each pair are preferably provided with substantially opposite curvilinear paths, preferable opposite helical paths, as will be described later in more detail. For example, wire 40a extends at least partially along a substantially counter-clockwise helical path while wire 40b extends at least partially along a substantially clockwise helical path. The four proximal pairs of wires are preferably separated by a uniform angle $\alpha_1$, which in this embodiment with four pairs of wires is about 90°.

Figure 3:
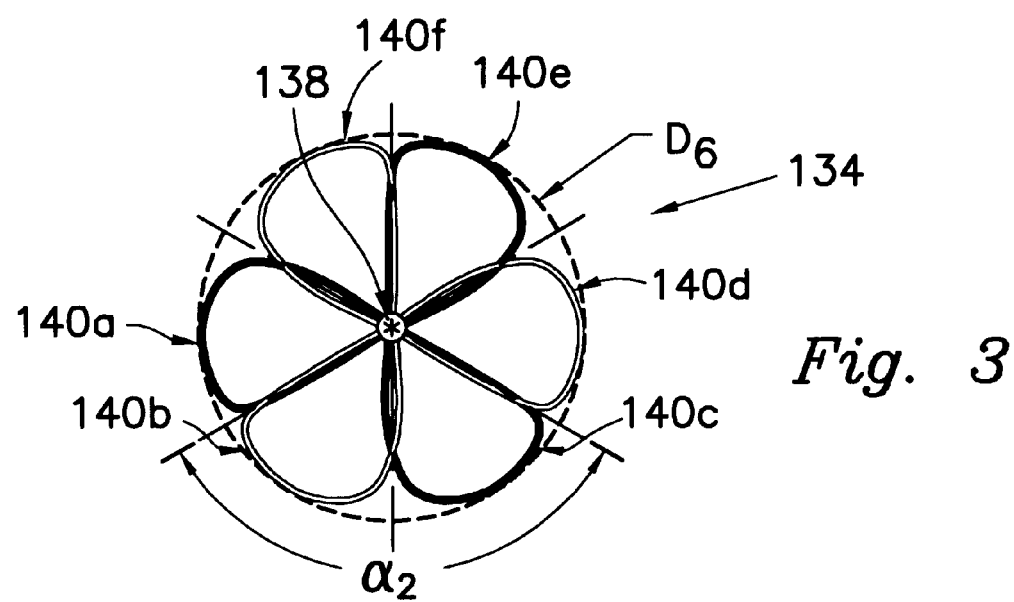
FIG. 3 shows a distal end view of another embodiment of a retrieval basket according to this invention.

FIG. 3 illustrates an alternative embodiment of a retrieval basket 134 that includes six wires 140a–140f that are preferably grouped into one of three pairs at the proximal end (e.g., wires 140a and 140b, wires 140c and 140d, and wires 140e and 140f). Like retrieval basket 34, retrieval basket 134 includes a rounded basket tip 138 and the wires are formed in such a way that they extend outwardly to a maximum achieved diameter $D_6$. The wires in each proximal pairing are preferably provided with substantially opposite helical paths, and the wire pairs are preferably separated by a uniform angle $\alpha_2$, which in the three-pair embodiment in FIG. 3 is about 120°.

Although eight-wire and six-wire embodiments have been illustrated in the Figures, it will be appreciated that other quantities of wires can be used to form the basket according to this invention. A ten-wire embodiment is clearly contemplated as are other even- or odd-numbered quantities of wires.

Figure 4:
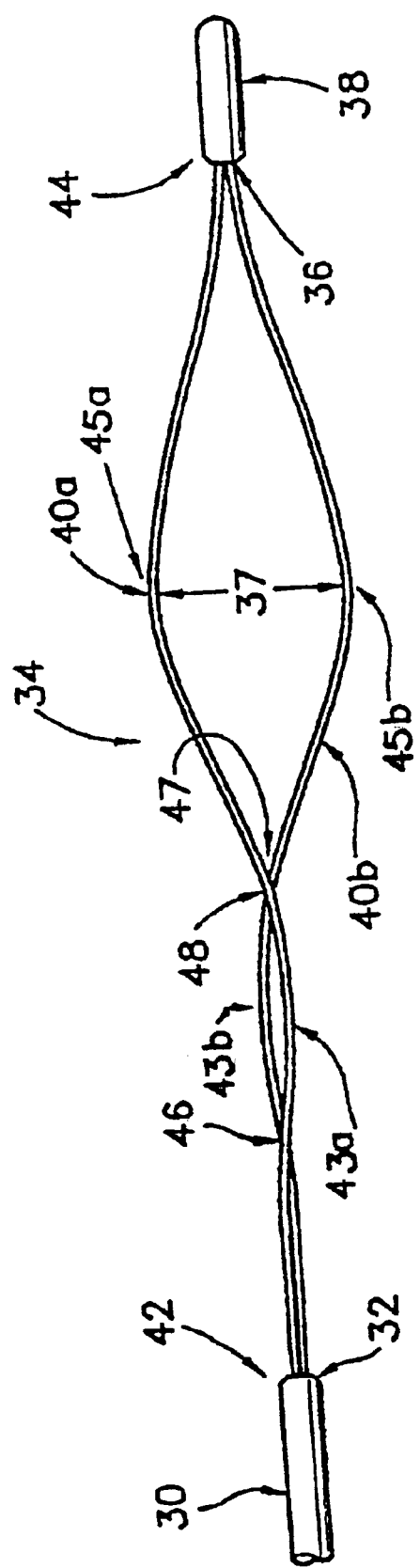
FIG. 4 shows a side view of a portion of the retrieval basket shown in FIGS. 1 and 2, illustrating preferred paths of two of the basket's wires.

FIG. 4 illustrates details of a portion of the retrieval baskets at 34 shown in FIG. 2 as defined by the view "V—V" in that figure. Only the pair of wires 40a and 40b is shown for the sake of clarity. Both of the wires 40a and 40b extend from a proximal end 42 of the basket to a distal end 44 of the basket. Wires 40a and 40b extend along a substantially straight path that diverges radially outwardly from the central longitudinal axis of the basket in a proximal portion of retrieval basket 34. In other words, in a proximal portion of the basket the wires can follow a path that is similar to that of the wires in a flat-wire basket. They simply ascend and diverge away from the basket's axis, without a significant degree of curvature with respect to the plane shared by the basket's axis, although some degree of wire curvature is expected in the proximal portion of the manufactured basket when it is in the expanded position, as will be described later. Wire 40a then extends along a curvilinear path such as a counter-clockwise helix toward the distal portion of the basket. In other words, in a distal portion of the basket the wires can follow a path that is similar to that of the wires in a helical basket. They descend and converge toward the basket's axis with a significant degree of curvature with respect to the plane occupied by the basket's axis.

As indicated in FIGS. 2 and 4, adjacent wires such as wires 40a and 40b, are preferably manufactured so that the curvatures in their respective distal portions are opposite or mirror images of one another such as in a clockwise helical direction (wire 40b) and a counter-clockwise direction (wire 40a). Accordingly, wire 40b extends in a substantially straight ascending path in the basket's proximal portion and then assumes a clockwise helix toward the basket's distal portion.

Wires 40a and 40b are preferably formed during the manufacturing process of the basket in order to have a virtually straight ascending portion of toward the proximal portion the basket that transitions into a descending helical path toward the distal portion of the basket. Nevertheless, when the retrieval basket 34 is in its expanded condition as shown in FIG. 2 and FIG. 4, the helix in the distal portion can be partially transferred from the distal portion into the proximal straight portion of the wires as the twisting forces and stresses in the wires are distributed along the basket's length. It has been discovered that this effect forms a unique "dual helix" or "dual helical path" configuration. The dual helix provides a helical wire path toward the proximal portion of the basket that has a curvature with a very large radius. In other words, the helix in the proximal portion has a very gentle pitch with a very small number of turns per unit length. This is contrasted with the helix toward the distal portion of the basket, which has a relatively tight curvature with a smaller radius and a tighter pitch with a larger number of turns per unit length.

The dual helix configuration can be seen in FIG. 4. In a proximal portion of basket 34 toward proximal end 42, wires 40a and 40b extend along a proximal helical path having a curvature with a relatively large radius. This large radius of curvature can be seen between and adjacent to the crossing points 46 and 48, which will be described in detail later. In contrast, wires 40a and 40b extend along a distal helical path having a curvature with a relatively small radius in a distal portion of basket 34 toward distal end 44. This smaller radius of curvature can be seen adjacent to crossing point 48 and extending to distal end 44. As seen in FIG. 4, each wire 40a and 40b includes at least two maximums 43a and 45a on wire 40a and 43b and 45b on wire 40b. These maximums are between proximal end 42 and distal end 44. Maximums 43a and 43b are in a proximal portion of basket 34 and maximums 45a and 45b are in a distal portion of basket 34. Each maximum is a point where wires 40a and 40b reach a maximum separation from one another.

Although a smooth curvature such as those illustrated in the Figures is preferred, wire kinks and bends can be used to shape the wires along a path having an overall curvature. For example, a multiplicity of small kinks or bends can be used to form one or more of the wires along a generally curvilinear path. Also, a single kink or bend or just a few kinks or bends can be used. For example, a kink or bend can be provided in the wire between a proximal curvature of larger radius and a distal curvature of smaller radius. Also, kinks or bends can be used in conjunction with smooth curves to form the path of one or more of the wires. Whether or not kinks, bends and/or smooth curves are utilized depends on the manufacturing technique selected and the desired basket performance characteristics.

It has been discovered that it is beneficial for wires 40a and 40b to be formed so that they extend from the basket's proximal end 42 closely adjacent to one another as opposed to all of the wires being evenly spaced from one another. In order to accomplish this, adjacent wires can be radially positioned at or near the proximal end of the basket so that they will extend from the proximal end next to one another before diverging.

The wire diverging point is preferably at the midsection of the basket but may also be proximal or distal to the midsection. Referring to FIG. 4, wires 40a and 40b diverge from one another at a diverging point 47. Preferably, the distance between proximal end 42 and diverging point 47 (length $L_3$ in FIG. 1) is at least about 40% of the distance between proximal end 42 and distal end 44 (length $L_5$ in FIG. 1), most preferably about 50% or more, although other proportions can be selected depending upon manufacturing considerations and the intended use of the basket. The exact or proportional distance of diverging point 47 is not critical to the invention.

The slight curvature that can be transferred to the proximal portion of the basket from the distal portion in the dual helix embodiment tends to cause adjacent wires such as wires 40a and 40b to cross at a first crossing point 46 as shown in FIG. 4 at a location near to proximal end 42. Subsequently, wires 40a and 40b cross back over one another at a second crossing point 48 before they diverge away from one another at diverging point 47. Although FIG. 4 illustrates an embodiment wherein wire 40a crosses in front of wire 40b at crossing points 46 and 48, wire 40b may instead cross in front of wire 40a at crossing points 46 and 48. Also, wires 40a and 40b can cross over and then behind one another; i.e., wire 40a can cross over wire 40b at crossing point 46 and then under wire 40b at crossing point 48, or wire 40b can cross over wire 40a at crossing point 46 and then under wire 40a at crossing point 48. Accordingly, wires 40a and 40b can be twisted or wrapped with respect to one another.

The crossing points 46 and 48 are not critical to the invention as will be described later with reference to FIG. 6. However, it has been discovered that the first and second crossing points 46 and 48 tend to provide contact points for mutual support between wires 40a and 40b and that such support actually serves to strengthen the retrieval basket 34. A crossing structure also tends to increase the radial dilatation force and radial opening force that can be exerted radially outwardly by the retrieval basket against an inner wall of a patient's duct such as a ureter. Increased dilatation force can be extremely beneficial to the performance of the basket and to the ease with which the retrieval basket is used because the basket can actually dilate the patient's duct at a location corresponding to a calculus so that it can be more easily surrounded by the basket.

Figure 5:
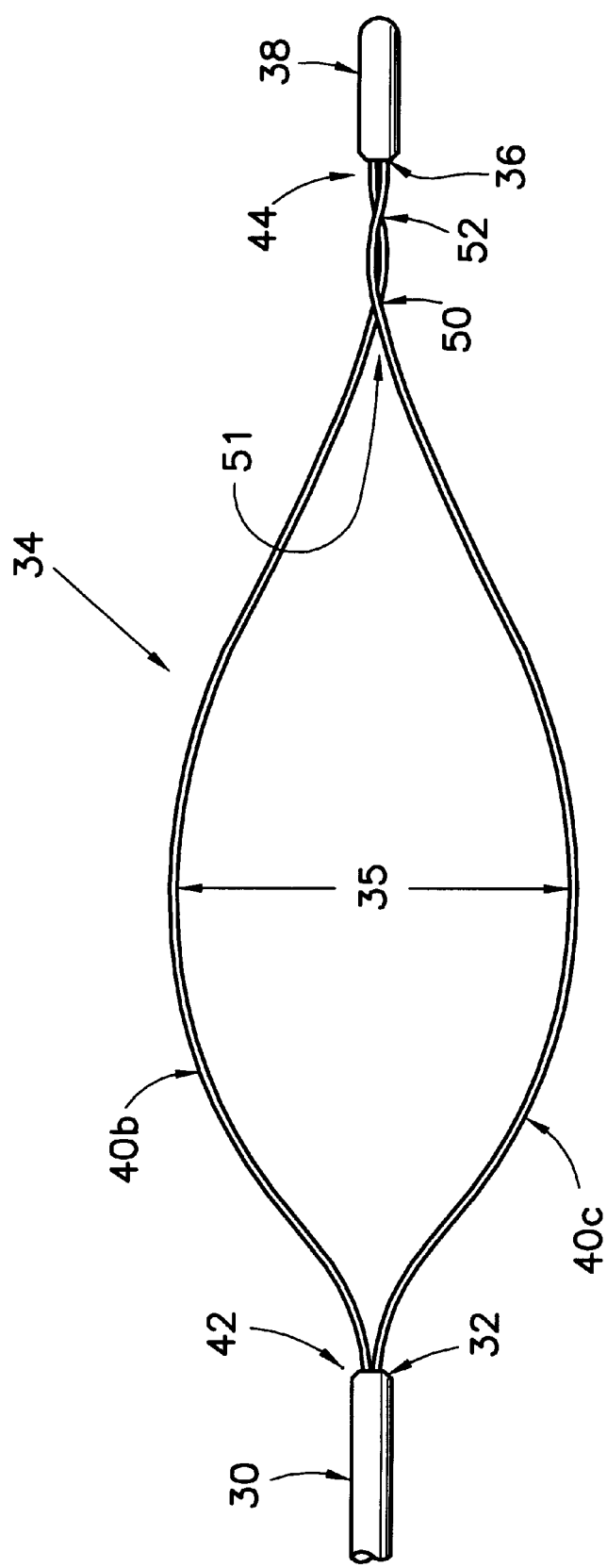
FIG. 5 shows another side view of a portion of the retrieval basket shown in FIGS. 1 and 2, illustrating preferred paths of two of the basket's wires.

FIG. 5 illustrates wires 40b and 40c that form a part of retrieval basket 34 as indicated in FIG. 2, and defined by the view "VI—VI" in FIG. 2. As with wires 40a and 40b, wires 40b and 40c extend from the basket's proximal end 42 in substantially straight paths that ascend radially outwardly away from the basket's axis, but wires 40b and 40c are positioned radially with respect to one another so that they separate or diverge away from one another from the start. Wires 40b and 40c later converge toward one another toward the distal portion of the basket as a result of their increased curvature in that portion. As shown in FIG. 5, they preferably cross one another at a first crossing point 50 and, most preferably, they subsequently cross back over one another at a second crossing point 52. Both crossing points 50 and 52 are near to the distal end of the basket. As with crossing points 46 and 48 of wires 40a and 40b, crossing points 50 and 52 tend to add strength to the retrieval basket 34 and to improve the dilatation force exertable by the basket when it is in its expanded position. As was described for crossing points 46 and 48, crossing points 50 and 52 can provide a twisting or wrapping configuration between wires 40b and 40c if wire 40b first crosses under and then over wire 40c or if wire 40c first crosses under and then over wire 40b.

As is made clear by reference to FIGS. 4 and 5, wires 40a and 40b are preferably positioned closely adjacent to one another as a pair in the proximal portion of the basket and define a relatively small space 37 (FIG. 4) at the distal portion of the basket through which calculi cannot easily pass. In contrast, the separation of wire 40b from wire 40c in the proximal region of the basket defines a larger gap 35 in that portion through which calculi can easily pass. Such a wider gap 35 near the proximal portion of retrieval basket 34 permits calculi to ingress with ease into the interior region of the expanded basket as the basket is drawn in the proximal direction to capture a calculus. It should also be noted that the size of gap 35 could also permit the intentional egress or deployment of a captured calculus from retrieval basket 34 upon the distal advancement of the basket in the expanded position if it is discovered that the captured calculus is too large in some dimension to be easily extracted from the patient.

The space 37 toward the distal end of retrieval basket 34 between wires 40a and 40b is significantly smaller in size as compared to gap 35 between wires 40b and 40c, thereby preventing the inadvertent escape of a calculus from the interior of the retrieval basket through space 37 as the basket is moved from its expanded position toward its collapsed position by manipulation with respect to the sheath in order to firmly capture the calculus. This is due in part to greater wire-calculi contact points for calculi entrapment and retention. At the same time, larger gap 35 facilitates the ingress of a calculus, or could facilitate the intentional deployment of the calculus, while the basket is expanded.

FIGS. 4 and 5 also illustrate that retrieval basket 34 is preferably asymmetrical along its length, which results in the significant disparity between the relative size of gap 35 as compared to space 37. As is illustrated in the figures, the distance between proximal end 42 of basket 34 and the second crossing point 48 between wires 40a and 40b is significantly larger than the distance between distal end 44 of basket 34 and the first crossing point 50 between wires 40b and 40c. Also, the length $L_3$ between proximal end 42 and diverging point 47 between wires 40a and 40b is significantly larger than the distance between a converging point 51 (FIG. 5) between wires 40b and 40c and distal end 44. It is this asymmetry, together with the relative radial positioning of the wires as they extend from the basket's proximal end, that is at least partially responsible for the size disparity between gap 35 and space 37. In other words, the positioning of crossing point 48 and diverging point 47 farther away from proximal end 42 reduces the size of distal space 37 between wires 40a and 40b and the positioning of crossing point 50 and converging point 51 closer to distal end 44 increases the size of proximal gap 35 between wires 40b and 40c.

Figure 6:
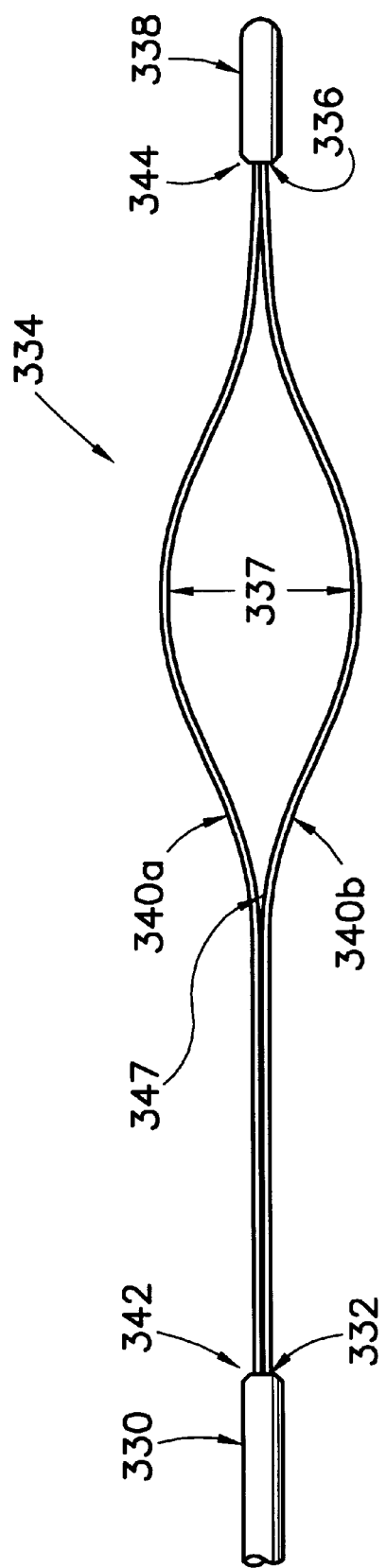
FIG. 6 shows a side view of a portion of another embodiment of a retrieval basket according to this invention, illustrating preferred paths of two of the basket's wires.

FIG. 6 illustrates another embodiment of a retrieval basket according to this invention, generally designated by the numeral "334". Like the others, this embodiment includes a connector tube 330 and solder joint 332 at proximal end 342 of the basket. Wires 340a and 340b corresponding generally in position to wires 40a and 40b (as shown in FIGS. 2 and 4) extend from the basket's proximal end 342 to a distal end 344. A solder joint connection 336 is made between the wires and a rounded basket tip 338.

Unlike the wires 40a and 40b shown in FIG. 4, adjacent wires 340a and 340b preferably never cross one another along the entire length of the basket. Instead, they extend from the basket's proximal end 342 generally parallel and closely adjacent to one another and in a substantially straight path as they ascend radially away from the basket's axis, only slightly separating sidewardly away from one another if at all as they extend longitudinally from the basket's proximal end 342. Although they are shown to be parallel and virtually touching in FIG. 6, it is clearly contemplated that wires 340a and 340b will separate from one another at a small angle to define a narrow "V" between them before they diverge. Farther along the basket and toward the basket's distal portion, wires 340*a* and 340*b* diverge sharply from one another at diverging point 347 along curved paths, such as helical paths, that are different from one another, preferably of opposite hands. The description of diverging point 47 with reference to FIG. 4 applies to diverging point 347 as well. Wires 340*a* and 340*b* can optionally be connected to one another at a point proximal of diverging point 347 to maintain their parallel configuration in the proximal portion of the basket.

The relative relationship between wire 340*b* and the next adjacent wire (not shown) corresponds closely to the relative relationship between wires 40*b* and 40*c* shown in FIG. 5. As will be noted from FIGS. 5 and 6, retrieval basket 334 enjoys the advantages of basket 34 in that large proximal gaps such as gap 35 are provided at the proximal portion of the retrieval basket 334 and a smaller distal space such as space 337 is provided toward the basket's distal end. This of course facilitates calculus ingress into the basket and firm calculus capture within the basket when the basket is closed around a calculus for extraction. It can also help to facilitate intentional calculus deployment from the basket when desired.

The only significant difference between baskets 34 and 334 is that basket 334 preferably does not include any crossing points between wires 340*a* and 340*b* near the proximal end of the basket. In fact, as shown in FIG. 4, wires 40*a* and 40*b* are very much like wires 340*a* and 340*b* in that they extend substantially parallel to one another in the basket's proximal portion.

The exact configuration of the wires of a retrieval basket according to this invention will vary according to the materials selected for the wires, the wire diameters selected and the method selected to form the wires into the shape of the retrieval basket. Although work-hardened 300 series stainless steel, nickel-titanium alloy, chromium-cobalt alloy and other similar materials are preferred materials for forming the wires, other suitable metallic or polymeric materials can be substituted. Also, although a wide variety of wire diameters and circular or non-circular cross-sectional shapes can be used, a diameter of about 0.007-inch has been found to form a flexible basket with an advantageous dilatation force, although other wire diameters may be beneficial for a particular application. As for the basket formation method, various methods are known in the art for forming wire baskets such as those described in Bates et al. U.S. Pat. No. 5,658,296, which is incorporated herein by reference.

Although the preferred basket embodiments illustrated in the figures include wires with helical paths in alternating directions, the wires can optionally follow substantially parallel yet diverging paths that may or may not cross one another. For example, the wires can follow relatively straight and parallel paths in the proximal portion of the basket and diverge into relatively helical and parallel paths in the distal portion.

It is contemplated that many additional variations and modifications to the embodiments selected for illustration in the drawings can be made without departing from the spirit or scope of the invention. Many features such as the selection of particular materials, dimensions, wire quantities and wire configurations are matters for the manufacturer's discretion and can vary from those described herein. The invention is described separately in the appended claims.

What is claimed is:

1. A retrieval basket adapted to capture calculi as it is moved along an axis of said retrieval basket in a proximal direction, said retrieval basket comprising:

a plurality of wires extending from a proximal end of said retrieval basket to a distal end of said retrieval basket wherein said wires converge toward one another at said proximal and distal ends, at least two of the wires forming a pair, each wire in the pair having relative to one another a first maximum in a proximal portion of the basket and a second maximum in a distal portion of the basket, the wires in the pair having at least two crossing points between the proximal and distal ends of the basket;

said wires in a proximal portion of said retrieval basket having a radius of curvature, and said wires in a distal portion of said retrieval basket having a radius of curvature, and wherein the radius of curvature of said wires in the proximal portion is smaller than that of said wires in the distal portion.

2. The retrieval basket defined in claim 1, wherein adjacent wires in said proximal portion extend from said proximal end closely adjacent one another and diverge from one another at a location that is spaced from said proximal end.

3. The retrieval basket defined in claim 2, wherein said adjacent wires cross one another adjacent to said proximal portion before diverging away from one another.

4. The retrieval basket defined in claim 3, wherein said adjacent wires cross one another at least two times adjacent to said proximal portion.

5. The retrieval basket defined in claim 2, wherein said adjacent wires extend substantially parallel to one another adjacent to said proximal portion before diverging away from one another.

6. The retrieval basket defined in claim 1, wherein said wires in the distal portion of said retrieval basket converge radially toward each other along relatively curvilinear paths, wherein said relatively curvilinear paths comprise substantially helical paths.

7. The retrieval basket defined in claim 6, wherein said helical path of at least one of said wires is oriented in a substantially opposite direction as compared to that of an adjacent wire.

8. The retrieval basket defined in claim 1, wherein adjacent wires in said distal portion cross one another adjacent to said distal portion.

9. The retrieval basket defined in claim 1, wherein said retrieval basket is positionable within a sheath to retain said retrieval basket in a collapsed position and is releasable from said sheath to expand said retrieval basket into an expanded position.

10. The retrieval basket defined in claim 9, wherein relative positions of said sheath and said retrieval basket are moveable with respect to one another along said axis of said retrieval basket.

11. The retrieval basket defined in claim 1, wherein at least one of said wires comprises a plurality of strands.

12. A surgical device adapted to capture calculi as it is moved along an axis in a proximal direction, said surgical device comprising:

a retrieval basket comprising a plurality of wires extending from a proximal end of said retrieval basket to a distal end of said retrieval basket wherein said wires converge toward one another at said proximal and distal ends, said wires in a proximal portion of said retrieval basket being inclined radially away from said axis of said surgical device along relatively straight paths, said wires in a distal portion of said retrieval basket converging radially toward said axis along relatively curvilinear paths, and wherein the radius of curvature of said relatively curvilinear paths is smaller than that of said relatively straight paths, at least two of the wires forming a pair, each wire in the pair having relative to one another a first maximum in a proximal portion of the basket and a second maximum in a distal portion of the basket, the wires in the pair having at least two crossing points between the proximal and distal ends of the basket;

a sheath positionable over at least a portion of said retrieval basket to maintain said retrieval basket in a collapsed position; and means for moving said retrieval basket and said sheath with respect to one another and for causing said retrieval basket to alternate between an expanded position and said collapsed position.

13. The surgical device defined in claim 12, wherein adjacent wires in said proximal portion extend from said proximal end closely adjacent one another and diverge from one another at a location that is spaced from said proximal end.

14. The surgical device defined in claim 13, wherein said adjacent wires cross one another adjacent to said proximal portion before diverging away from one another.

15. The surgical device defined in claim 13, wherein said adjacent wires extend substantially parallel to one another adjacent to said proximal portion before diverging from one another.

16. The surgical device defined in claim 12, wherein said wires in the distal portion of said retrieval basket converge radially toward each other along relatively curvilinear paths, wherein said relatively curvilinear paths comprise substantially helical paths.

17. The surgical device defined in claim 16, wherein said substantially helical paths of adjacent wires are oriented in a substantially opposite direction.

18. The surgical device defined in claim 12, wherein adjacent wires in said distal portion cross one another adjacent to said distal portion.

19. The surgical device defined in claim 12, wherein said moving means comprises a shaft connected to said retrieval basket and extending proximally from said retrieval basket.

20. The surgical device defined in claim 19, wherein at least a portion of said shaft is flexible.

21. The surgical device defined in claim 12, wherein at least one of said wires comprises a plurality of strands.

22. A retrieval basket for use with a surgical device, said retrieval basket being adapted to capture calculi as it is moved along an axis in a proximal direction, said retrieval basket comprising:

a plurality of wires extending from a proximal end of said retrieval basket to a distal end of said retrieval basket wherein said wires converge toward one another at said proximal and distal ends, at least two wires forming a pair having at least two crossing points between the proximal and distal ends of the basket;

wherein said wires extend along substantially helical paths between said proximal end and said distal end of said retrieval basket, wherein said wires in a proximal portion of said retrieval basket extend along a proximal helical path and said wires in a distal portion of said retrieval basket extend along a distal helical path, wherein said distal helical path has a smaller radius of curvature as compared to said proximal helical path.

23. The retrieval basket defined in claim 22, wherein adjacent ones of said wires extend from said proximal end closely adjacent one another and diverge from one another at a location that is spaced from said proximal end.

24. The retrieval basket defined in claim 23, wherein said adjacent wires in said proximal portion cross one another adjacent to said proximal portion before diverging away from one another.

25. The retrieval basket defined in claim 22, wherein said helical paths of adjacent wires are oriented in a substantially opposite direction.

26. The retrieval basket defined in claim 22, wherein adjacent ones of said wires in said distal portion cross one another adjacent to said distal portion.

27. The retrieval basket defined in claim 22, wherein said retrieval basket is positionable within a sheath to retain said retrieval basket in a collapsed position and is releasable from said sheath to expand said retrieval basket into an expanded position.

28. The retrieval basket defined in claim 27, wherein relative positions of said sheath and said retrieval basket are moveable with respect to one another along said axis of said retrieval basket.

29. The retrieval basket defined in claim 22, wherein at least one of said wires comprises a plurality of strands.

30. In a surgical extractor for removing an object from a surgical patient, said surgical extractor including a plurality of wires surrounded by a sheath in a retracted position and forming a basket for retrieving said object in an expanded position, said basket including a proximal end portion and a distal end portion, the improvement wherein said basket comprises pairs of wires, wherein said wires in each of said pairs extend adjacent to one another in said proximal end portion of said basket to define a space between adjacent pairs, and wherein said wires in each of said pairs diverge from one another toward said distal end portion of said basket and toward a wire of the adjacent pair, at least two of the wires forming a pair, each wire in the pair having relative to one another a first maximum in a proximal portion of the basket and a second maximum in a distal portion of the basket, and each wire in the pair having at least two crossing points between the proximal and distal ends of the basket.

31. A retrieval basket adapted to capture calculi as it is moved along an axis of said retrieval basket in a proximal direction, said retrieval basket comprising:

a plurality of wires extending from a proximal end of said retrieval basket to a distal end of said retrieval basket wherein said wires converge toward one another at said proximal and distal ends;

said wires in a proximal portion of said retrieval basket being inclined radially away from said axis of said retrieval basket along relatively straight paths, said wires in a distal portion of said retrieval basket converging radially toward said axis along relatively curvilinear paths, and wherein the radius of curvature of said relatively curvilinear paths is smaller than that of said relatively straight paths; and wherein adjacent wires in said proximal portion extend from said proximal end closely adjacent one another and diverge from one another at a location that is spaced from said proximal end; and wherein the adjacent wires form a pair having two crossing points between the proximal and distal ends of the basket.

32. The retrieval basket defined in claim 31, wherein said adjacent wires cross one another adjacent to said proximal portion before diverging away from one another.

33. The retrieval basket defined in claim 32, wherein said adjacent wires cross one another at least two times adjacent to said proximal portion.

34. A retrieval basket adapted to capture calculi as it is moved along an axis of said retrieval basket in a proximal direction, said retrieval basket comprising:

a plurality of wires extending from a proximal end of said retrieval basket to a distal end of said retrieval basket wherein said wires converge toward one another at said proximal and distal ends;

said wires in a proximal portion of said retrieval basket being inclined radially away from said axis of said retrieval basket along relatively straight paths, said wires in a distal portion of said retrieval basket converging radially toward said axis along relatively curvilinear paths, and wherein the radius of curvature of said relatively curvilinear paths is smaller than that of said relatively straight paths; and wherein two of said wires form a pair having at least two crossing points between the proximal and distal ends of the basket;

wherein said relatively curvilinear paths comprise substantially helical paths.

35. The retrieval basket defined in claim 34, wherein said helical path of at least one of said wires is oriented in a substantially opposite direction as compared to that of an adjacent wire.

36. A retrieval basket adapted to capture calculi as it is moved along an axis of said retrieval basket in a proximal direction, said retrieval basket comprising:

a plurality of wires extending from a proximal end of said retrieval basket to a distal end of said retrieval basket wherein said wires converge toward one another at said proximal and distal ends;

said wires in a proximal portion of said retrieval basket being inclined radially away from said axis of said retrieval basket along relatively straight paths, said wires in a distal portion of said retrieval basket converging radially toward said axis along relatively curvilinear paths, and wherein the radius of curvature of said relatively curvilinear paths is smaller than that of said relatively straight paths;

wherein adjacent wires in said distal portion cross one another adjacent to said distal portion; and wherein the adjacent wires form a pair having two crossing points between the proximal and distal ends of the basket.

37. A surgical device adapted to capture calculi as it is moved along an axis in a proximal direction, said surgical device comprising:

a retrieval basket comprising a plurality of wires extending from a proximal end of said retrieval basket to a distal end of said retrieval basket wherein said wires converge toward one another at said proximal and distal ends, said wires in a proximal portion of said retrieval basket being inclined radially away from said axis of said surgical device along relatively straight paths, said wires in a distal portion of said retrieval basket converging radially toward said axis along relatively curvilinear paths, and wherein the radius of curvature of said relatively curvilinear paths is smaller than that of said relatively straight paths;

a sheath positionable over at least a portion of said retrieval basket to maintain said retrieval basket in a collapsed position;

means for moving said retrieval basket and said sheath with respect to one another and for causing said retrieval basket to alternate between an expanded position and said collapsed position;

wherein adjacent wires in said proximal portion extend from said proximal end closely adjacent one another and diverge from one another at a location that is spaced from said proximal end; and wherein the adjacent wires form a pair having two crossing points between the proximal and distal ends of the basket.

38. The surgical device defined in claim 37, wherein said adjacent wires cross one another adjacent to said proximal portion before diverging away from one another.

39. The surgical device defined in claim 37, wherein said adjacent wires extend substantially parallel to one another adjacent to said proximal portion before diverging from one another.

40. A surgical device adapted to capture calculi as it is moved along an axis in a proximal direction, said surgical device comprising:

a retrieval basket comprising a plurality of wires extending from a proximal end of said retrieval basket to a distal end of said retrieval basket wherein said wires converge toward one another at said proximal and distal ends, said wires in a proximal portion of said retrieval basket being inclined radially away from said axis of said surgical device along relatively straight paths, said wires in a distal portion of said retrieval basket converging radially toward said axis along relatively curvilinear paths, and wherein the radius of curvature of said relatively curvilinear paths is smaller than that of said relatively straight paths;

a sheath positionable over at least a portion of said retrieval basket to maintain said retrieval basket in a collapsed position;

means for moving said retrieval basket and said sheath with respect to one another and for causing said retrieval basket to alternate between an expanded position and said collapsed position;

wherein said relatively curvilinear paths comprise substantially helical paths; and wherein two wires form a pair having at least two crossing points between the proximal and distal ends of the basket.

41. The surgical device defined in claim 40, wherein said substantially helical paths of adjacent wires are oriented in a substantially opposite direction.

42. A surgical device adapted to capture calculi as it is moved along an axis in a proximal direction, said surgical device comprising:

a retrieval basket comprising a plurality of wires extending from a proximal end of said retrieval basket to a distal end of said retrieval basket wherein said wires converge toward one another at said proximal and distal ends, said wires in a proximal portion of said retrieval basket being inclined radially away from said axis of said surgical device along relatively straight paths, said wires in a distal portion of said retrieval basket converging radially toward said axis along relatively curvilinear paths, and wherein the radius of curvature of said relatively curvilinear paths is smaller than that of said relatively straight paths;

a sheath positionable over at least a portion of said retrieval basket to maintain said retrieval basket in a collapsed position;

means for moving said retrieval basket and said sheath with respect to one another and for causing said retrieval basket to alternate between an expanded position and said collapsed position;

wherein adjacent wires in said distal portion cross one another adjacent to said distal portion; and wherein the adjacent wires form a pair having two crossing points between the proximal and distal ends of the basket.

43. A retrieval basket having a plurality of wires adapted to capture cacluli as it is moved along an axis of said retrieval basket in a proximal direction, said retrieval basket comprising:

at least one pair of adjacent wires each having a distal portion and a proximal portion, the distal portion including a section extending along a proximal path in a first radius of curvature;

said wires having a proximal portion including a section extending along a second radius of curvature, and wherein said first radius of curvature is different from the second radius of curvature, each radius of curvature lying in a separate plane; and wherein two wires form a pair having at least two crossing points between the proximal and distal ends of the basket.

44. The retrieval basket of claim 43, wherein adjacent wires in said proximal portion extend from said proximal end closely adjacent one another and diverge from one another at a location that is spaced from said proximal end.

45. The retrieval basket of claim 43, wherein said adjacent wires cross one another adjacent to said proximal portion for diverging away from one another.

46. The retrieval basket of claim 45, wherein said adjacent wires cross one another at least two times adjacent to said proximal portion.

47. The retrieval basket of claim 43, wherein the wires follow a helical path.

48. The retrieval basket of claim 47, wherein the first radius of curvature is larger than the second radius of curvature.

49. The retrieval basket of claim 48, wherein said helical path of at least one of said wires is oriented in a substantially opposite direction as compared to that of an adjacent wire.

50. The surgical device of claim 48, wherein said wires are closely adjacent and cross one another adjacent to said proximal portion before diverging away from one another.

51. The surgical device of claim 50, wherein said adjacent wires extend substantially parallel to one another adjacent to said proximal portion before diverging from one another.

52. The surgical device of claim 47, wherein said substantially helical path of adjacent wires are oriented in a substantially opposite direction.

53. The retrieval basket of claim 43, wherein the first radius of curvature is larger than the second radius of curvature.

54. A retrieval basket adapted to capture calculi as it is moved along an axis of said retrieval basket in a proximal direction, said retrieval basket comprising:

a plurality of wires extending from a proximal end of said retrieval basket to a distal end of said retrieval basket wherein said wires converge toward one another at said proximal and distal ends, at least two of the wires each having relative to one another a first maximum in a proximal portion of the basket and a second maximum in a distal portion of the basket;

said wires in a proximal portion of said retrieval basket having a radius of curvature, and said wires in a distal portion of said retrieval basket having a radius of curvature, and wherein the radius of curvature of said wires in the proximal portion is smaller than that of said wires in the distal portion;

wherein adjacent wires in said proximal portion extend from said proximal end closely adjacent one another and diverge from one another at a location that is spaced from said proximal end;

wherein said adjacent wires cross one another adjacent to said proximal portion before diverging away from one another; and wherein said adjacent wires cross one another at least two times adjacent to said proximal portion.

55. A retrieval basket adapted to capture calculi as it is moved along an axis of said retrieval basket in a proximal direction, said retrieval basket comprising:

a plurality of wires extending from a proximal end of said retrieval basket to a distal end of said retrieval basket wherein said wires converge toward one another at said proximal and distal ends;

said wires in a proximal portion of said retrieval basket being inclined radially away from said axis of said retrieval basket along relatively straight paths, said wires in a distal portion of said retrieval basket converging radially toward said axis along relatively curvilinear paths, and wherein the radius of curvature of said relatively curvilinear paths is smaller than that of said relatively straight paths;

wherein adjacent wires in said proximal portion extend from said proximal end closely adjacent one another and diverge from one another at a location that is spaced from said proximal end;

wherein said adjacent wires cross one another adjacent to said proximal portion before diverging away from one another; and wherein said adjacent wires cross one another at least two times adjacent to said proximal portion.

56. A retrieval basket having a plurality of wires adapted to capture cacluli as it is moved along an axis of said retrieval basket in a proximal direction, said retrieval basket comprising:

at least one pair of adjacent wires each having a distal portion and a proximal portion, the distal portion including a section extending along a proximal path in a first radius of curvature;

said wires having a proximal portion including a section extending along a second radius of curvature, and wherein said first radius of curvature is different from the second radius of curvature, each radius of curvature lying in a separate plane;

wherein adjacent wires in said proximal portion extend from said proximal end closely adjacent one another and diverge from one another at a location that is spaced from said proximal end;

wherein said adjacent wires cross one another adjacent to said proximal portion for diverging away from one another; and wherein said adjacent wires cross one another at least two times adjacent to said proximal portion.

* * * * *